(12) United States Patent
Hayes et al.

(10) Patent No.: US 8,821,703 B2
(45) Date of Patent: Sep. 2, 2014

(54) SYSTEM AND METHOD FOR AUTOMATED BIOPARTICLE RECOGNITION

(76) Inventors: Mark A. Hayes, Scottsdale, AZ (US); Thomas J. Taylor, Tempe, AZ (US); Karl Booksh, Scottsdale, AZ (US); Neal Woodbury, Scottsdale, AZ (US); Pierre Herckes, Scottsdale, AZ (US)

( * ) Notice: Subject to any disclaimer, the term of this patent is extended or adjusted under 35 U.S.C. 154(b) by 1169 days.

(21) Appl. No.: 12/667,944

(22) PCT Filed: Jul. 7, 2008

(86) PCT No.: PCT/US2008/008334
§ 371 (c)(1),
(2), (4) Date: May 3, 2011

(87) PCT Pub. No.: WO2009/009028
PCT Pub. Date: Jan. 15, 2009

(65) Prior Publication Data
US 2011/0201511 A1    Aug. 18, 2011

Related U.S. Application Data

(60) Provisional application No. 60/958,643, filed on Jul. 6, 2007.

(51) Int. Cl.
*B03C 5/02*    (2006.01)
*C40B 30/04*    (2006.01)
*C40B 60/12*    (2006.01)

(52) U.S. Cl.
USPC .................. 204/547; 204/643; 506/9; 506/39

(58) Field of Classification Search
None
See application file for complete search history.

(56) References Cited

U.S. PATENT DOCUMENTS

| 7,455,966 B1 * | 11/2008 | Schaudies et al. | 435/6.1 |
| 2002/0006653 A1 * | 1/2002 | Meyers et al. | 435/193 |
| 2004/0072278 A1 * | 4/2004 | Chou et al. | 435/29 |
| 2005/0227222 A1 * | 10/2005 | Braun et al. | 435/4 |
| 2007/0207555 A1 * | 9/2007 | Guerra et al. | 436/518 |

FOREIGN PATENT DOCUMENTS

WO    WO 2005/063962    *    7/2005

* cited by examiner

*Primary Examiner* — Anne Gussow
*Assistant Examiner* — Channing S Mahatan

(57) ABSTRACT

The invention relates to a method for identifying the source of shed bioparticles and an apparatus that implements the method. The method involves collecting a sample of bioparticles from the environment, selecting from that sample the bioparticles most effective in identifying their source, and gathering data from those bioparticles to form bioparticle signatures. The bioparticle signatures are then processed into a multi-dimensional vector which is then compared to the multi-dimensional vector derived from a standard using a pattern recognition strategy that identifies the source. The apparatus has a particle collection device to collect the sample, a transfer device that selects information-rich bioparticles and a detector that restricts the movement of the information-rich bioparticles. The restricted movement is then translated into a bioparticle signature.

7 Claims, 8 Drawing Sheets

FIG. 2

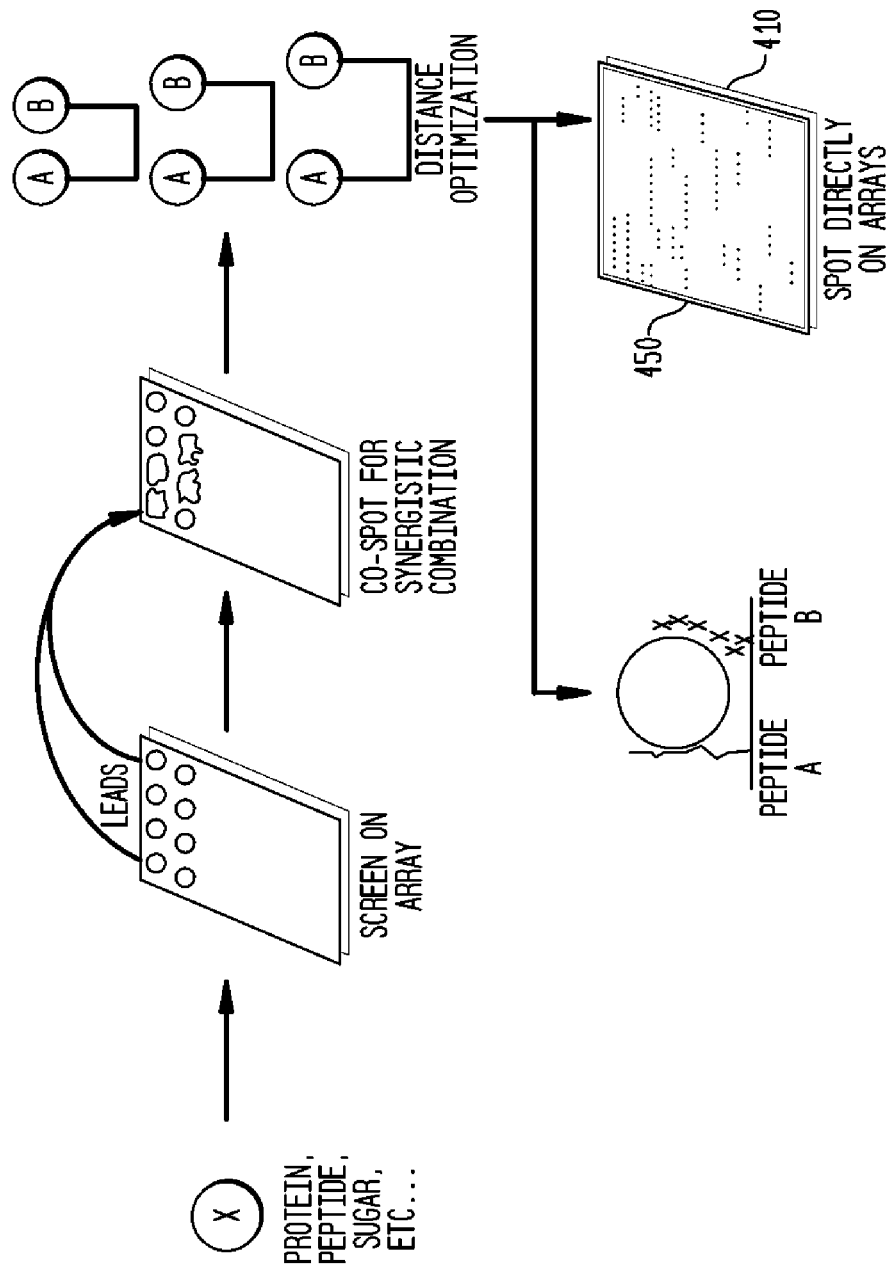

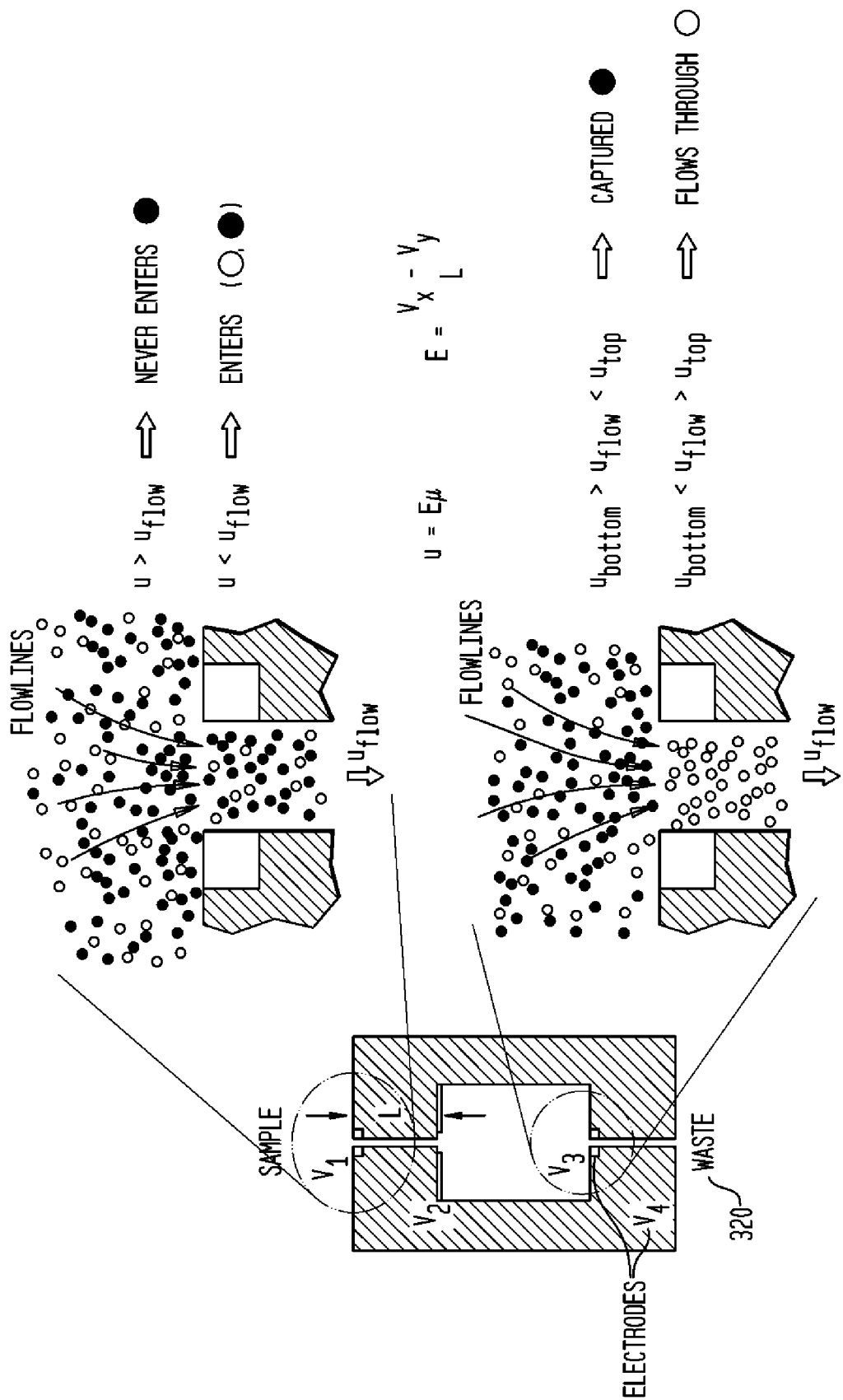

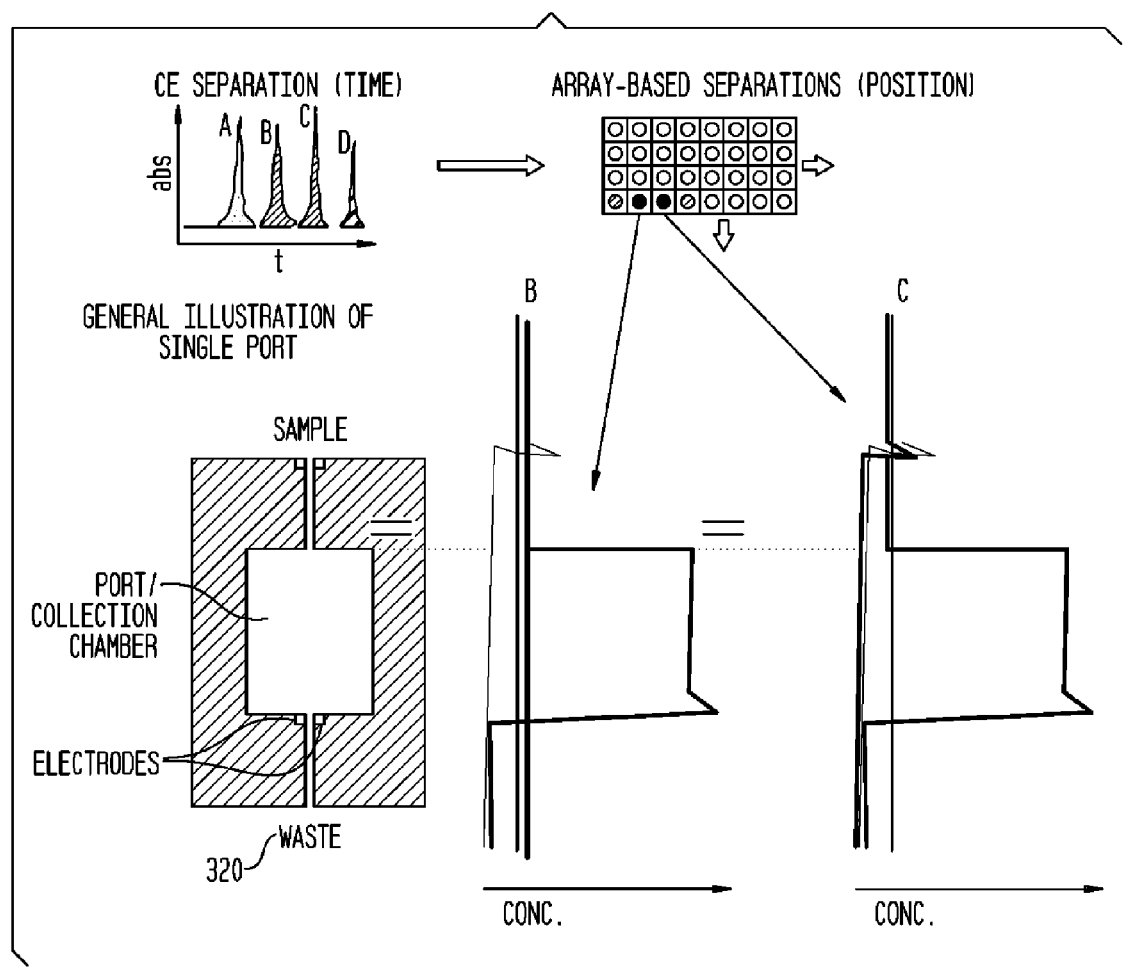

SYSTEM AND METHOD FOR AUTOMATED BIOPARTICLE RECOGNITION

FIELD OF THE INVENTION

The present invention relates to the field of automated bioparticle recognition systems and methods, and more specifically to the collection of bioparticles and analysis of bioparticle signatures.

BACKGROUND OF THE INVENTION

Bioparticles are biological materials shed from an organism. Compared to volatile compounds, bioparticles are generally present in greater quantities than volatile compounds, last longer in the environment, may be detected at lower levels, and provide a great breadth of physical or biological information. For example, many organisms including humans shed millions of skin flakes per minute, and each sneeze results in thousands of fine droplets of fluid. These settle slowly in the air and contain biological information potentially relevant to the identification of the individual. Bioparticles may be identified as being from a particular source which may then indicate the former or current presence of that source.

Identification of a biological source from evidence consisting of such bioparticles has relied upon forensic genetics based on polymorphism. However, forensic genetics based on polymorphism has utilized only a limited portion of DNA (deoxyribonucleic acid) polymorphism and has been based on low-effective techniques such as differential electromobility studies. Forensic DNA analysis, which includes analysis of restriction fragment length polymorphisms, PCR (polymerase chain reaction) analysis of variable number terminal repeats, and PCR analysis of short tandem repeats, requires the presence of high quality, intact DNA for a robust result. As shown, current methodology in forensic genetics is hindered by exacting requirements or low-effective techniques.

Even more, much of the matter released from an individual is made up of enucleated cells from the stratum corneum that have undergone apoptosis and hair shafts without any attached cellular material. Since these materials are nearly devoid of high-quality, intact DNA, DNA-based analysis of such bioparticles is of little use for identifying individuals. In addition, the scarce amount of DNA that may be present in these materials has typically undergone fragmentation in the process of apoptosis. Furthermore, even if a high-quality sample is present, it typically requires amplification by PCR. This, in turn, is problematic in that performing a PCR reaction is labor intensive, slow, and subject to false positive readings due to cross-contamination of other human DNA.

Other methods of identifying these bioparticles include the use of labeled reagents to selectively (i.e., specifically) target biological materials. The labeled reagents selectively bind to a biological target and emit a signal that indicates the presence of the material. The specific binding is typically achieved by use of any of a variety of biological probes, most notably proteins, including antibodies, antibody fragments, short peptides, and natural receptors for the component; carbohydrates; lipoproteins; and lipids known to be naturally specific for or created to be specific for a particular component of the material. Examples of molecules that send a signal include synthetic or naturally fluorescent molecules, enzymes that act upon a substrate to change it in an observable way, metal particles that allow labeled cells to be seen in a microscope or separated with a magnet, and radioactive isotopes. However, labeled reagents are typically costly, require special storage conditions, such as refrigeration, and may be slow in yielding meaningful data.

Methods that identify individuals based upon the release of shed materials without the need for DNA amplification or labeled reagents have relied upon the collection of volatile compounds, such as pheromones, cellular breakdown products, and the like. However, methods for the detection of volatile compounds suffer from several limitations, including the fact that volatile compounds are typically released from organisms in low concentrations, the volatile compounds of the organism can be confused with volatile compounds already present in the environment, and volatile compounds tend to disperse rapidly into the environment.

In view of the above, there is a need for a method to identify individuals based upon shed material and which avoids the difficulties and limitations of the methods currently practiced in the art.

SUMMARY OF THE INVENTION

It is an object of the invention to identify a particular source of bioparticles shed into the environment.

It is another object of the invention to identify the particular source of shed bioparticles as originating from a human being as opposed to other mammals.

It is another object of the invention to identify the particular source of shed bioparticles as originating from one particular human being out of a group of other human beings.

It is another object of the invention to identify the particular source of shed bioparticles as having recently been present in a particular geographical area.

It is another object of the invention to identify a particular source of shed bioparticles using bioparticles that are in an aerosol form.

It is another object of the invention to identify a particular source of shed bioparticles using particles shed from the stratum corneum of the skin.

It is another object of the invention to identify a particular source of shed bioparticles using hair and hair degradation products as the shed bioparticles.

It is another object of the invention to identify a particular source of shed bioparticles using bacterial flora as the shed bioparticles.

It is another object of the invention to identify a particular source of shed bioparticles by comparing the bioparticle signatures from the collected bioparticles to a database of known bioparticle signatures.

It is another object of the invention to identify a particular source of shed bioparticles by comparing the bioparticle signatures from the collected bioparticles to signatures of bioparticles having a known source.

It is another object of the invention to identify a particular source of shed bioparticles by comparing the bioparticle signatures from the collected bioparticles to those collected from a particular geographical location.

It is another object of the invention to select and transfer information-rich bioparticles by diverting them from a flowing solution using an electric field.

It is another object of the invention to restrict the movement of information-rich bioparticles through dielectrophoretic separation in order to generate a bioparticle signature from said information-rich bioparticles.

It is another object of the invention to localize information-rich bioparticle fractions through dielectrophoretic concentration.

It is another object of the invention to shunt information-rich bioparticle fractions for further analysis.

It is another object of the invention to analyze information-rich bioparticle fractions through biochemical extraction followed by detection of their chemical components.

It is another object of the invention to detect chemical components of bioparticle fractions through further dielectrophoretic separation and/or binding to a panel of peptides or antibodies.

It is another object of the invention to utilize detected patterns of separation and/or binding to characterize species, individuals, and individual biochemistry.

It is another object of the invention to ascertain a source's state of health by assessing the bioparticles shed from the source.

It is another object of the invention to identify the presence of an individual by detecting shed bioparticles in an aerosol form.

In an embodiment, the above objectives are achieved by a method comprising:

(i) collecting a plurality of bioparticles from the environment;

(ii) selecting an information-rich bioparticle or information-rich bioparticle fraction from the plurality of bioparticles;

(iii) as part of the process for detecting a bioparticle signature from the information-rich bioparticle, restricting the movement of the information-rich bioparticle or information-rich bioparticle fraction;

(iv) processing a plurality of said bioparticle signatures into a multi-dimensional vector; and (v) identifying the biological source based upon comparison of said multi-dimensional vector to a standard multi-dimensional vector or vectors using a pattern recognition strategy.

The invention is also directed to an apparatus for practicing the method set forth herein, the apparatus comprising:

a particle collector configured to collect a sample containing a plurality of bioparticles;

a selection and concentration system coupled to the particle collector configured to select an information-rich bioparticle or bioparticles from the plurality of bioparticles;

a bioparticle signature detector coupled to the selection and concentration system, the bioparticle signature detector comprising means for restricting the movement of the information-rich bioparticles and means for detecting a plurality of bioparticle signatures therefrom; and a pattern recognition system linked to the bioparticle signature detector and configured to derive a multi-dimensional vector from the bioparticle signatures and compare said multi-dimensional vector with a standard multi-dimensional vector or vectors in order to identify the biological source.

BRIEF DESCRIPTION OF THE FIGURES

A more complete understanding of the present invention can be provided by referring to the following illustrative figures as further explained in the detailed description section. However, the invention is not in any way limited to the embodiments shown in the figures.

FIG. 2 depicts an embodiment of the invention with sub-components.

FIG. 7 depicts the process of generation of one form of a panel of compounds.

FIG. 8 depicts an embodiment of the portal system and a process by which information-rich bioparticles are separated from a bioparticle sample.

FIG. 9 depicts another embodiment of the invention along with examples of readouts from surface plasmon resonance detection.

DETAILED DESCRIPTION OF THE INVENTION

Figure 1:
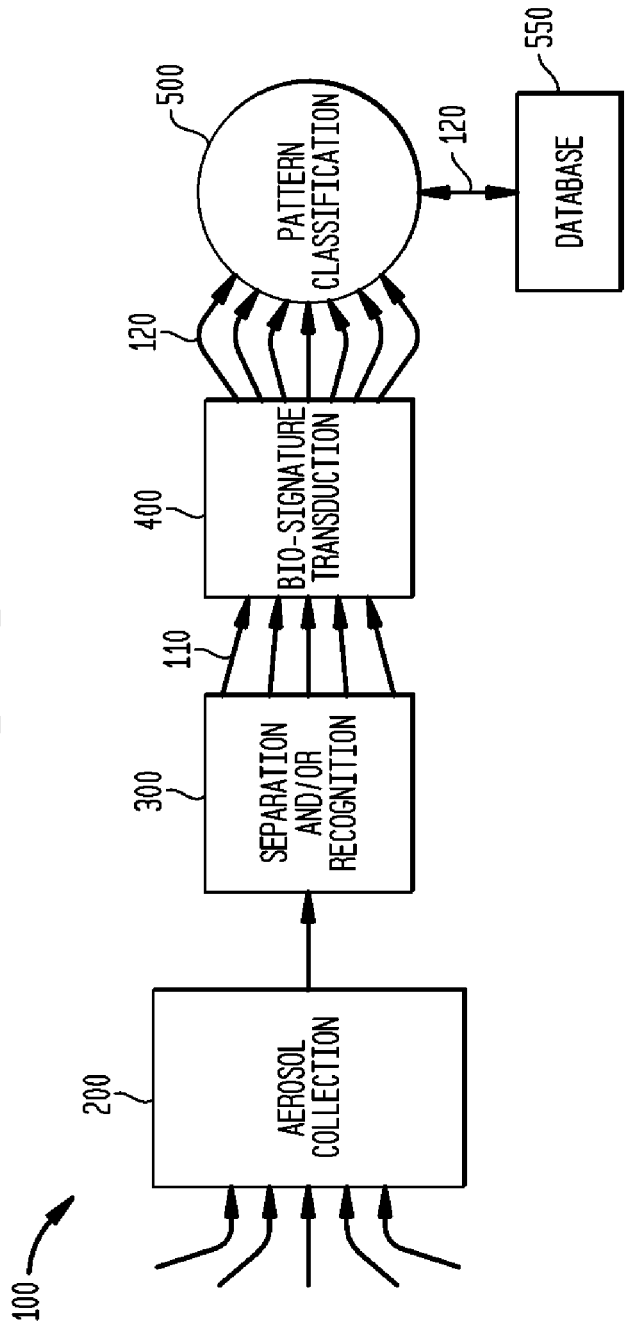
FIG. 1 depicts a diagram of an embodiment of the process with numbers indicating the components that perform each process.
Figure 3:
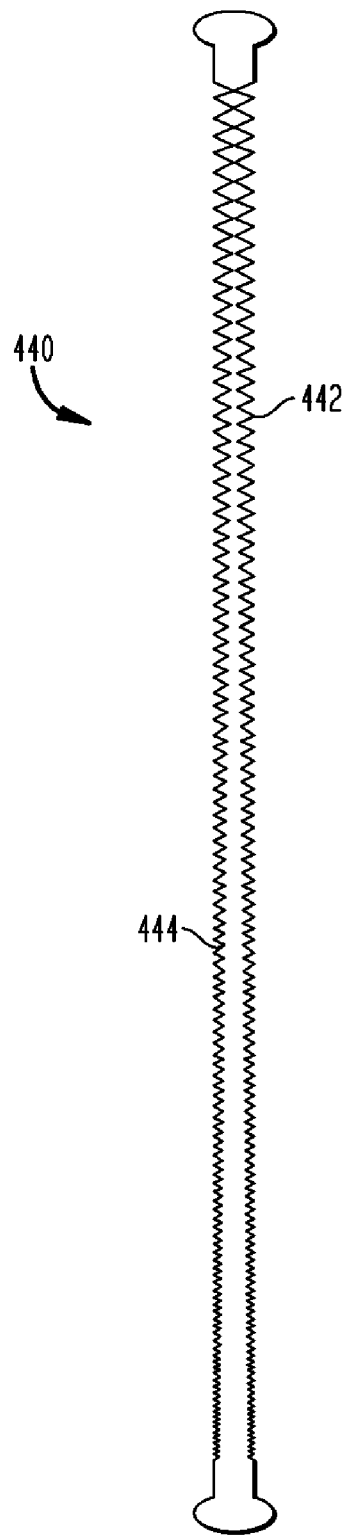
FIG. 3 depicts an embodiment of the dielectrophoresis chamber with two different sections that allow concentration of different particles in different sections.
Figure 4:
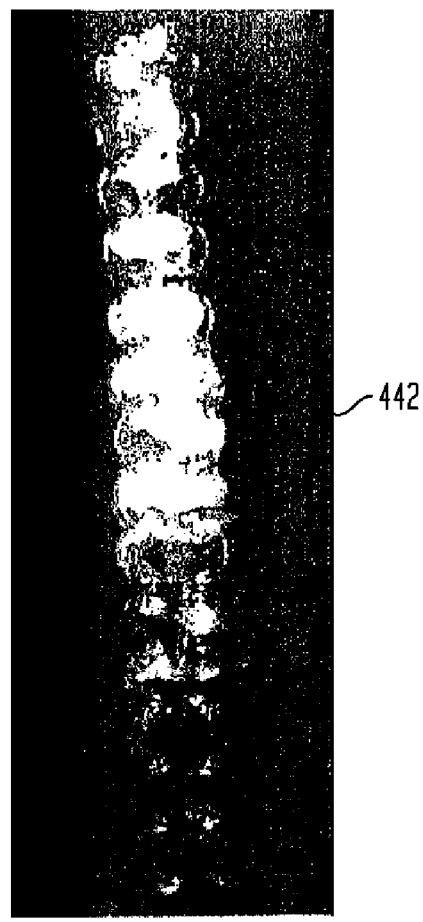
FIG. 4 depicts a section of the dielectrophoresis chamber from FIG. 3 in which live *Bacillis subtilis* bacteria have been concentrated.
Figure 5:
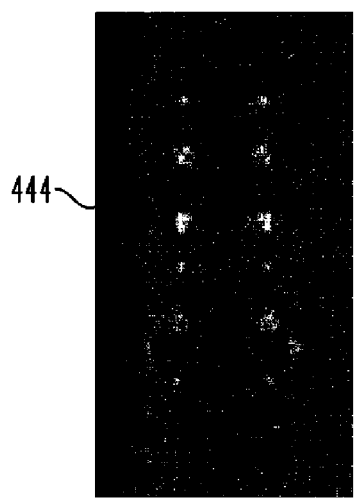
FIG. 5 depicts a section of the dielectrophoresis chamber from FIG. 3 in which dead *Bacillis subtilis* bacteria have been concentrated.
Figure 6:
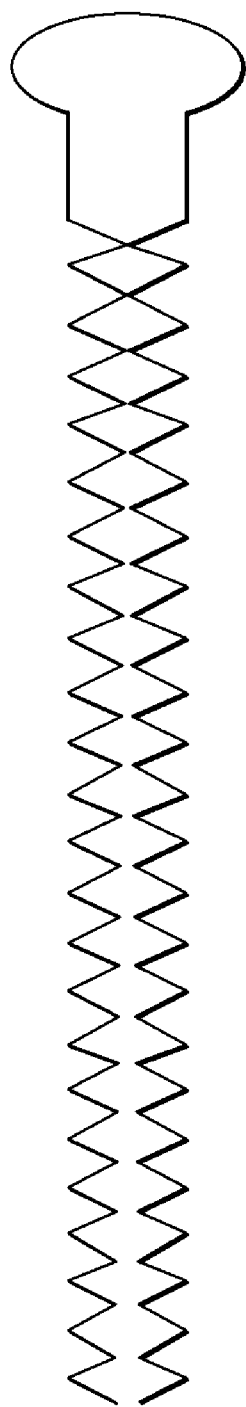
FIG. 6 depicts a close up of the dielectrophoresis chamber from FIG. 3 to show details of the insulating elements.

In one aspect, the invention is directed to a method for identifying a biological source. The biological source can be any organism, and more typically, any mammal. More typically, the biological source is one (i.e., individual) or more human beings.

In the method, a plurality of bioparticles (i.e., shed particulates) are first collected from the environment. The environment from which the bioparticles are collected can be any type of environment, including, for example, gaseous (i.e., airborne or aerosol bioparticles), liquid (e.g., bioparticles on or suspended within a liquid), or solid or semi-sold (e.g., bioparticles on the surface of, or within, a solid or semi-solid). The bioparticles are collected by any suitable means. In a preferred embodiment, the bioparticles are collected by a particulate collection system. The particulate collection system can comprise any of the collection systems known in the art. For example, the particulate collection system may comprise a wet cyclone, impact collector, electrostatic collector, or the like.

The bioparticles can be any material shed from an organism and is typically biological in nature. The bioparticles can be classified according to any of the general biological classes of materials. For example, the bioparticle can be proteinaceous (e.g., a protein, peptide, or antibody), nucleic acid-containing (e.g., a nucleobase, nucleotide, oligonucleotide, or nucleic acid), lipid-containing (e.g., fatty acid-containing), steroidal, one or more small biological molecules, other types of biological material, and combinations thereof. Some more specific examples of bioparticles include cells (e.g., skin-derived or epidermis cells), protein structures, hair, pathogenic and non-pathogenic bacterial, viral, fungal, protozoal or other organisms, and plant-derived material (e.g., pollen). Shed material from the skin is particularly plentiful and includes particles from the outer skin layer (e.g., stratum corneum) and other skin layers that contain keratin. Though the bioparticles are largely organic, they may also be inorganic. For example, the bioparticle can be a mineral, such as talc. The bioparticle also need not be natural in composition, but may be synthetic (e.g., particulates used in cosmetics or other toiletries). Often, the bioparticles are constructed of aggregations of molecules or other bioparticles. Such aggregations include cells, viruses, pollen grains, skin flakes, hair, bacteria, and several other types of aggregations of organic and inorganic molecules.

After collection of the bioparticles, one or more information-rich bioparticles (i.e., "an information-rich bioparticle") are selected from the plurality of bioparticles and transferred to a bioparticle signature detector (i.e., "the detector"). The information-rich bioparticles are selected by any means known in the art. In a preferred embodiment, a voltage source is used for selecting and transferring a bioparticle of interest to the detector. The present invention also contemplates transferring a bioparticle of interest by known electric, magnetic or flow fields. It is understood in accordance with the present invention that certain bioparticles may be common to all samples and therefore may be non-distinguishing. Other bioparticles will vary from sample to sample and therefore will be indicative of those samples. Once the sample composition is well characterized and understood, only bioparticles which are distinguishing are selected and processed for physical, chemical or biochemical assessment. After a bioparticle has been selected, it is transferred to the detector where a bioparticle signature is detected. A bioparticle signature is a collection of data derived from a bioparticle that is characteristic of that bioparticle. Several bioparticle signatures may be combined to identify the source of the bioparticles. Bioparticle signatures include any data that may be derived from the analysis of bioparticles and includes the molecular weight, charge, acidity, hydrophobicity, or structure of any organic or inorganic chemical or the sequence of any protein that is a component of the bioparticle.

The methods and apparatus disclosed herein use a plurality of bioparticle signatures comprising individual characteristics or measurements, or a group of multiple characterizations or measurements, or combinations thereof. The term bioparticle signature includes any optical, physical or chemical measurement which can contribute to providing a unique identifying element of the sample. The source of the bioparticles may be identified to varying levels of specificity depending upon the data and number of bioparticle signatures analyzed. These levels of specificity include identifying the source as a particular species relative to all other species, or as a particular individual of a species as opposed to other individuals within that species. The bioparticle signatures may also identify a source by discerning a particular metabolic process over other metabolic processes A plurality of bioparticle signatures can be generated from a bioparticle by a number of methods. In accordance with the present invention, a bioparticle signature can be generated from an optical, physical and/or chemical measurement or combination thereof. In one embodiment, a bioparticle signature is generated by first restricting or sequestering the movement of the bioparticle. The movement of the bioparticle can be restricted or sequestered by any suitable means, such as, for example, by use of an electrical field, a physical flow, field gradient, isoelectric focusing, and various mass spectrometry methods or combinations thereof.

In a particular embodiment, the information-rich bioparticle is conventionally restricted or sequestered by binding to a panel of compounds, e.g., antibodies or peptides, including peptides prescreened for affinity to the bioparticle source. The peptides can be generated by, for example, phage display. Other types of compounds which would interact with and bind or sequester bioparticles include but are not limited to monomeric compounds, polymeric compounds, aptamers, small molecules and the like. Such binding partners are well known and appreciated by the skilled artisan.

In another embodiment, the movement of a bioparticle is restricted by methods that utilize electrophoresis or dielectrophoresis. The dielectrophoretic separation can be achieved by any suitable means known in the art. For example, dielectrophoretic separation can be achieved by placing insulators into the electrophoretic field. Some other methods known in the art for accomplishing dielectrophoresis include flow separation, field-flow fractionation, stepped flow fractionation, traveling wave dielectrophoresis, ratcheting mechanisms including thermal ratchets and stacked ratchets, and rotational dielectrophoresis, streaming dielectrophoresis, and trapping dielectrophoresis. See, for example, Hughes, M. P., et al., "Strategies for dielectrophoretic separation in laboratory-on-a-chip systems," *Electrophoresis,* 23(16) 2569-2582, (2002), the contents of which are herein incorporated by reference.

Once the movement of the bioparticle is restricted, a unique bioparticle signature for the restricted bioparticle can be detected using any suitable method, such as any spectroscopic, electrochemical, mass spectroscopic or physical measurement. In a preferred embodiment, a unique bioparticle signature for the restricted bioparticle is detected by use of surface plasmon resonance (SPR) on the restricted bioparticle. Any suitable type of SPR technique can be used herein. For example, the SPR technique can be a label-free and/or capillary electrophoresis SPR technique. Surface plasmon resonance is a phenomena of differential reflectance of light from a metallic gold-fluid interface depending on the frequency of the light and the fluid density within a few wavelengths of the surface; a shift in the density, e.g. from a binding particle or protein at the surface is detectable as intensity change in reflected monochromatic light. It is a commonly used method for detecting biomolecules, see, e.g. G. Ramsey, Commercial Biosensors: Applications to Clinical, Bioprocess, and Environmental Samples (John Wiley and Sons, New York, 1998) or H. Raether, "Surface Plasmons on Smooth and Rough Surfaces and on Grating" (Springer-Verlag, New York, 1988).

The plurality of bioparticle signatures is then processed into a multi-dimensional vector. In accordance with the present invention, any measurement resulting in at least one magnitude constitutes an informational vector. Such informational vectors can constitute an intensity of an array spot or a particular magnitude at a given retention time. All optical, physical and chemical measurements will generate informational vectors. When such informational vectors are combined into data set reflecting the sample, they can be described as "multi-dimensional vector" or "tensor" in accordance with the present invention.

The multi-dimensional vector, thus obtained, is then compared with a standard multi-dimensional vector using a pattern recognition strategy in order to identify the biological source. A standard may be derived from a database or a single known source of bioparticles, including a geographical location. In accordance with the present invention, a multidimensional vector can be considered as defining a location in multidimensional space. A set of such vectors, each vector associated to a single sample of bioparticles with known relationships to species, lineages, individuals known or unknown or places, constitutes a collection of standards. Collectively, this set of standards defines overlapping regions in multidimensional space, wherein the positioning of data from a multidimensional vector in a region implies a statistical relationship with a species, lineage or individual or place, much as a forensic DNA match may specify identity. A number of pattern recognition methods are known in the art and incorporated herein. Some well-known specific pattern recognition methods include those defined on page 21 (infra).

In another aspect, the invention is directed to an apparatus useful for accomplishing the method described above. The apparatus includes means for accomplishing each of the steps described above. For example, the apparatus includes means for collecting a sample containing a plurality of bioparticles, i.e., by use of a particle collector. All commercially available particle collectors are contemplated by the present invention.

A preferred sampling system is the Omni 3000 by Sceptor Industries. However, the invention also contemplates applications which require design of specialized sampling systems. The apparatus also includes means, coupled to the particle collector, configured to select an information-rich bioparticle from the plurality of bioparticles. For example, the means for selecting an information-rich bioparticle can be a "selection and concentration system," which includes a portal configured to divert the information-rich bioparticle from a directional flow of a solution containing the plurality of bioparticles. Preferably, the portal is configured to divert the information rich bioparticle with an electromagnetic field.

The apparatus also includes a bioparticle signature detector coupled to the selection and concentration system described above. The bioparticle signature detector preferably includes means for restricting the movement of the information-rich bioparticles, by any of the means described above, and means for detecting a plurality of bioparticle signatures therefrom. In one embodiment, the detector includes a dielectrophoresis chamber for restricting movement of the information-rich bioparticle. The dielectrophoresis chamber preferably includes an element placed within an electromagnetic field (for example, an insulator or a protuberance extending from the wall of the chamber into the electromagnetic field). Such chambers are well recognized in the art. See e.g., the following references, all of which are incorporated hereby reference: Pysher, M. D. & Hayes, M. A., "Electrophoretic and Dielectrophoretic Field Gradient Technique for Separating Bioparticles" *Analytical Chemistry* 79(12): 4552-4557 (2007); Lapizco-Encinas, B. H., Simmons, B. A., Cummings, E. B. & Fintschenko, Y., "Insultor-Based Dielectrophoresis for the Selective Concentration and Separation of Live Bacteria in Water" *Electrophoresis,* 25:1695-1704 (2004); Lapizco-Encinas, B. H., Simmons, B. A., Cummings, E. B. & Fintschenko, Y., "Dielectrophoretic Concentration and Separation of Live and Dead Bacteria in an Array of Insulators", *Anal. Chem.* 76:1571-1579 (2004); Lapizco-Encinas, B. H., Davalos, R. V., Simmons, B. A., Cummings, E. B. & Fintschenko, Y., "An Insulator-Based (Electrodeless) Dielectrophoretic Concentrator for Microbes in Water", *Journal of Microbiological Methods,* 62:317-326 (2005). In another embodiment, the detector includes a panel of compounds for restricting movement of the information-rich bioparticle. The panel of compounds can be, for example, a peptide, an antibody binding domain, or molecules generated by phage display.

In a preferred embodiment, the means for detecting bioparticle signatures is by use of a surface plasmon resonance (SPR) detector. The SPR detector can be any suitable SPR detector, but is more preferably a label-free or capillary electrophoresis SPR detector.

The apparatus also includes a pattern recognition system linked or coupled to (i.e., in communication with) the bioparticle signature detector and configured to produce (i.e., derive) a multi-dimensional vector from the bioparticle signatures. The pattern recognition system also preferably includes means for comparing the multi-dimensional vector, as produced, with a standard multi-dimensional vector, as described above, in order to identify the biological source.

Referring to FIG. 1, an embodiment of the process for identifying the source of a shed bioparticle is depicted. The process comprises collecting a sample of bioparticles 100 using a particulate collection system 200. Selected bioparticles 110 are pulled out of the sample of bioparticles 100 using a selection and concentration system 300. Data from the selected particles is used to generate bioparticle signatures which are then processed into multi-dimensional vectors 120 by the detector 400. A pattern recognition system 500 then compares the multi-dimensional vectors 120 with multi-dimensional vectors from previously collected samples stored in a database 550.

Referring to FIG. 2, the particulate collection system 200 may comprise a wet cyclone, impact collector, or electrostatic collector, among others. The bioparticles 100 may be collected by the particulate collection system 200 from the air, but they may also be collected from a surface, a fluid, any surface within a fluid, and from films, mud, or the interior of otherwise solid objects. Bioparticles may be concentrated into a solution which serves to concentrate the bioparticles, facilitates their transfer to the selection and concentration system 300, and, optionally, to alter the bioparticles 100 to facilitate downstream analysis. The bioparticles 100 may be altered through enzymatic digestion into smaller components or other methods, including manipulation of pH, salinity, heat or the detergent content of the solution. The solution may comprise an acidic, basic, neutral, or buffered solution. The bioparticles 100 may be transferred through a microfluidic pump 310 to the selection and concentration system 300; however, the transfer can also be accomplished by use of a peristaltic pump, syringe, capillary tube, or an automatic or manual pipettor. A portal 320 powered by a voltage source 321 serves to select a bioparticle 110 from the solution and transfer it to the detector 400 that contains a surface capable of making measurements by surface plasmon resonance 410. Separation within the detector is powered by a voltage source 402. Other aspects of the portal 320 are depicted in FIGS. 8 and 9.

The selected bioparticles 110 are captured at the entrance to the potential field of the portal. Bioparticles 100 that carry a charge move at a velocity defined by flow of solution until they reach the potential field. The potential field may act on a range of species whose electromigration rates are greater than the flow rate so as to generate a focusing effect. The flow and potentials may be tuned, adjusted, calibrated, programmed or manipulated so as to capture, focus, concentrate, specify or divert any bioparticle target. The tool may be scaled up or down in size. A portal 320 may be independently and dynamically tuned to capture a specific species of interest. Further, each portal 320 may be adjusted to a predetermined range of target concentration, significantly extending the dynamic range. This process is depicted graphically in FIG. 8.

There are many advantages to this selection and concentration system 300, including: immediate initiation of the separation at each portal 320, allowing patterns for each target to begin to form when the flow and electric field are initiated, thus avoiding the development time of standard separation systems; convective transport driven into each portal 320 so development time is not dependent on diffusion alone; selectivity for a particular type of bioparticle or bioparticle component at each portal 320; an adjustable electric field that allows the array to be reprogrammed such that different bioparticles 100 may be selected by the same portal 320; and the ability to probe the same sample for several patterns by simple readjustment of the electric field at each portal 320. Further, each portal 320 may be set to collect all or a small portion of a particular species creating a large dynamic range, so that high abundance species can be quantitatively measured in parallel to low abundance species. If the features of adjustable targets and variable dynamic range or target concentration are combined, this allows for an active pattern matching capability. If a particular known sample state is present, the entire array may be programmed to directly match those species and concentrations to generate a single "flat" output.

Figure 2:
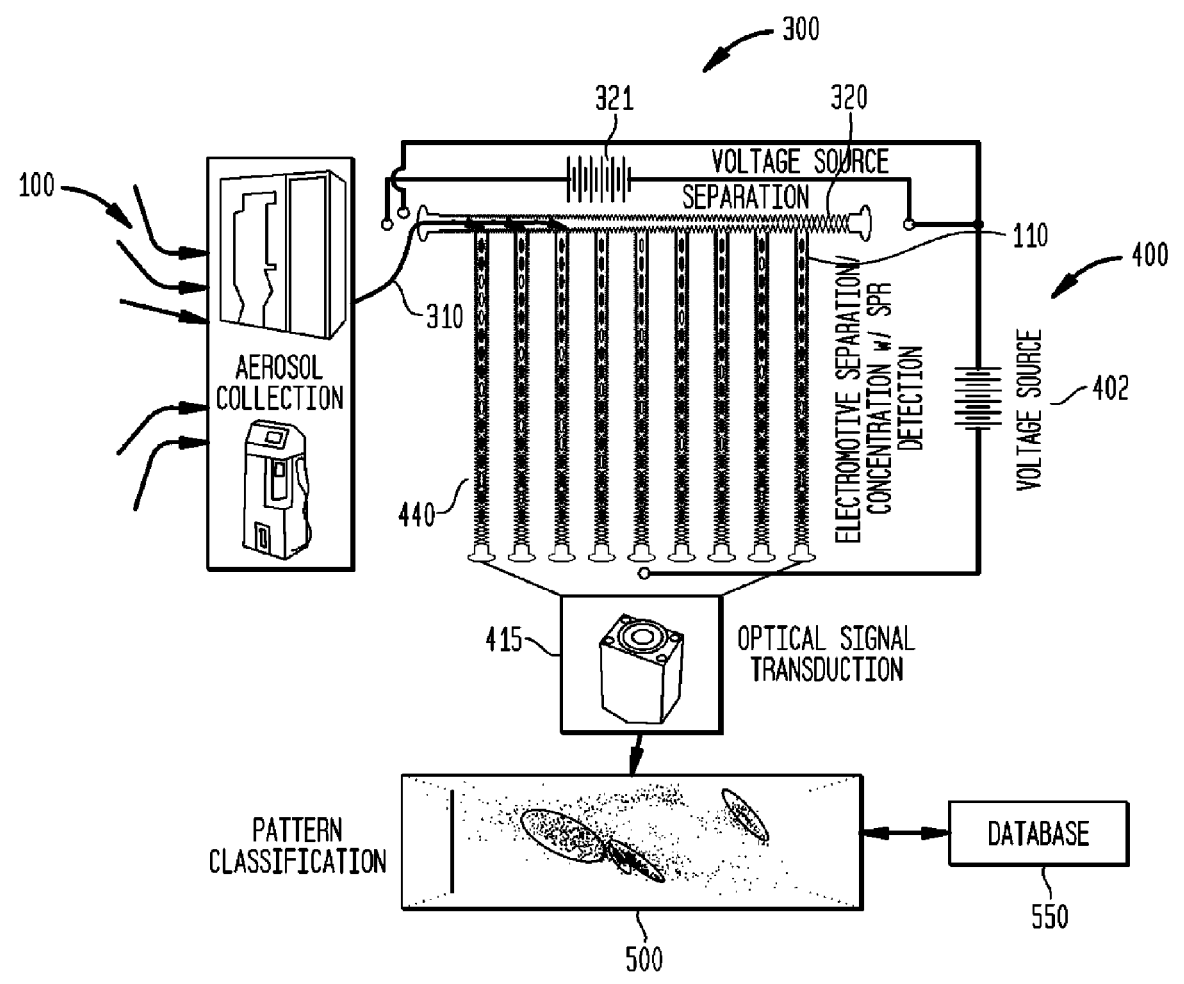

In the form of the invention depicted in FIG. 2, the detector 400 acts upon a selected bioparticle 110 to restrict its movement so as to generate a pattern that is specific for the selected bioparticle 110 and to use surface plasmon resonance to detect the pattern. The detector 400 may act to restrict the movement of the selected bioparticle 110 in any of a number of ways, including electrophoresis, isoelectric focusing, and various mass spectrometry methods. Data is generated with a label-free surface plasmon resonance detection (SPR) surface 410 and read by an optical sensor 415. The SPR sensing surface may be combined with capillary electrophoresis as an end of column detector 410. In this combination, the SPR sensing surface is embedded within the detector 400 and loss and dilutions of selected bioparticles 110 at the SPR sensor may be prevented, allowing for quantitative analysis. However, other methods may be used for generating the data, including fluorescence quenching measurements, detection of native fluorescence of aromatic residues present on the bioparticle, and one and two-dimensional gel electrophoresis.

As shown in FIG. 2, the detector 400 restricts the movement of the selected bioparticle 110 by subjecting it to dielectrophoresis. Variability in the gradient of the electric field relative to the selected bioparticle 110 may be achieved by placing of insulators, resistors, or conductors within the field, by embedding electrodes within the apparatus oriented such that they can alter the direction of the field, or by other similar methods. In this form of the invention, variability in the electric field gradient is achieved using insulators.

The insulators may be incorporated as part of the shape of the wall of the electrophoresis chamber, either formed together with or separately from the walls. The insulators may also be independent from the walls and fixed in place or movable in order to provide a method of focusing, concentrating, or coordinating the movement of the selected bioparticle. An insulator may be formed of Lucite, other plastic, Pyrex or other glass, or any other suitable resistant material.

Referring to FIGS. 3 and 6, in one form of the dielectrophoresis chamber 440, a plurality of insulators 446 is incorporated into the wall of the dielectrophoresis chamber 440. Referring to FIG. 3, the selected bioparticle 110 enters the interior of the dielectrophoresis chamber 440. The insulators 446 restrict the motion of the selected bioparticle 110 to create a pattern of electrophoretic migration. The degree of restriction of motion is measured by a surface plasmon resonance detector 410. The shape of the wall of the dielectrophoresis chamber 440 serves to define, spatially, the location of a selected bioparticle or to concentrate a selected bioparticle 110.

The shape of the wall shown in FIG. 3 may be uniform or non-uniform throughout the dielectrophoresis chamber 440. The walls of the dielectrophoresis chamber 440 are shaped in such a way that insulators incorporated into the wall 420 alter the electric field. In one form of the invention, the insulator 420 is saw-tooth shaped, but it may also be bulbous, square, in the form of a sine wave, or in any other configuration that is capable of altering the electrical field. The spacing and intensity of the isopotential gradients within the dielectrophoresis chamber 440 is a function of the size, geometry, orientation and spacing of the insulators 420. A form of a dielectrophoresis chamber 440 using the shape of the wall to introduce insulators 446 into the electrical field to concentrate a selected bioparticle is displayed in FIG. 6.

By judiciously choosing the size and orientation of the insulators 420, the isopotential gradients can be engineered to capture a specific bioparticle. One aspect of this concept is demonstrated in FIGS. 3, 4, and 5. A section of the dielectrophoresis chamber 440 with more pronounced wall features 442 is capable of concentrating live *Bacillis subtilis* bacteria as shown in FIG. 4. A section of the dielectrophoresis chamber with less pronounced wall features 444 concentrates dead *Bacillis subtilis*. A mixture of live and dead cells was stained with a dye that causes green fluorescence in living cells. They were then added to the dielectrophoresis chamber and voltage was applied.

By varying the size, shape, and orientation of the wall features, different classes of selected bioparticles 110 can be trapped in different areas and concentrated. Further separation can be obtained by applying other separation conditions to the selected bioparticle 110 including pH gradients, ion concentration gradients, detergent concentration gradients, matrices such as gels, and heating protocols based upon time and temperature. In another form of the invention, the detector 400 restricts the movement of the selected bioparticle 110 by exposing it to a panel of compounds 450. One way to generate the panel of compounds 450 is depicted in FIG. 7. The detector 400 restricts the movement of a selected bioparticle 110 by binding it to a panel of compounds 450 with a signal generated by a surface capable of measuring surface plasmon resonance 410 in response to binding of the selected bioparticle 110 to the panel of compounds 450. The panel of compounds 450 may comprise a peptide, but could also comprise a carbohydrate, adhesion molecule, lipoprotein, lipid, alternative protein scaffold, aptamer, small organic molecule, whole protein, and the like. A whole protein could include an antibody or antibody fragment with linear or conformational binding epitopes, natural receptors or ligands, and any domains or fragments derived from any of these. The library may be generated by phage display, but may also be generated by ribosome display, cellular display, protein fragment complementation assay or SELEX, among other methods.

The panel of compounds 450 may be generated by the selection of molecules previously optimized to bind with a selected bioparticle 110 known to emanate from the source of the selected bioparticle 110. The optimization process may include screening a randomly generated peptide library for peptides for that bind to the selected bioparticle 110 and selecting a combination of peptides that together generate a binding interaction with higher avidity.

Referring back to FIGS. 1 and 2, signals from the detector 400 generate bioparticle signatures which are in turn processed into multi-dimensional vectors 120. The multidimensional vectors can be used to identify a bioparticle source via one or more pattern classification and/or recognition methods. These methods include Binary Tree classifiers, (multi-layer) Neural Network classifiers, Bayesian Network classifiers, Support Vector Machine classifiers, Gaussian Process classifiers, k-Nearest Neighbour classifiers and Gaussian Mixture Model classifiers, among others (see Duda R., et al., *Pattern Classification*, John Wiley & Sons, New York © 2001, the contents of which are incorporated by reference herein).

The pattern recognition method compares the multi-dimensional vector 120 of bioparticle signatures associated with a sample against multi-dimensional vectors 120 from samples collected previously. Any number of previously collected samples, including a single sample can be used to generate multi-dimensional vectors 120 for comparison. The multi-dimensional vector 120 may contain numerical measurements of micro-particulate properties, such as size, charge, surface properties, dielectric character, and polarizability of bioparticles as well as differential or actual affinities to a panel of compounds 450. The multi-dimensional vector 120 includes a combination of the response of each individual component contained in the collection from the substrate, with a representation of the relative concentration of each component in the substrate. These representations include linear, graphical, or any of a variety of electronic data representations.

The process of training the device includes collecting data labeled according to type. Signal processing of a sample may include the following; identifying information-rich portions of the signal for optimal data complexity/accuracy tradeoff, determining the signal distortion characteristics of the device, extracting a set of ideal bioparticle signatures that encompass the training data potentially including background and target information-rich portions, characterizing the abundance distribution of the different information rich portions in the training data and the confidence associated with these estimates, classifying a new sample for absence or presence of various types of animal, plant, fungal or microbial activity, determining the temporal course of these activities, and cross-comparing distinguishing features of the new sample against features of samples from other locations.

The system that implements the pattern classification/recognition 500 may be linked to the device by wire or wireless linkages. Some examples of wireless linkages include infrared, microwave, visible, internet, satellite, and others. The system may be present with and/or coupled to the device or it may operate remotely from the device. Multi-dimensional vectors 120 from a specific individual or location can be compared with and/or contrasted against a biometric/geographic database 550 that includes multi-dimensional vectors 120 previously collected from one or more individuals or locations. Such a database 550 may compare information gathered from a location of interest to information gathered from a standard. The standard may be anything that aids in the identification of the source of the bioparticle signature including a standard for identifying a particular source or a background for a specific location. The standard may be inclusive of or exclusionary as to the source.

A multi-dimensional vector 120 can indicate the amount of time that has passed since the source of the bioparticles left the area. Bioparticles 100 are subject to modification and decomposition by the environment, for example including digestion by organisms, oxidation, reduction, and photodegradation, among other factors. For example, bioparticles may be digested first by fungi (e.g., including *Aspergillus Repens*) and then by dust mites. These digestions typically occur in predictable (i.e., regular or characteristic) ways, and are in part dependent upon the time that has passed since the source was present at a particular location. Since decomposition of the bioparticles alters the bioparticle signature in a characteristic way, the alteration can be detected by the means described above. This, in turn, allows a measurement of the amount of time a bioparticle has resided in a particular location.

The method described above can also be used to identify a location which had been in contact with (i.e., visiting by) a particular source. In one embodiment, to establish a location as having been visited by the source, bioparticles from a particular location are tested to determine if their signatures match those of bioparticles identified with a particular source. Alternatively, a location is established as having been visited by a source by collecting particles from the source and testing these particles to determine if their signatures match those of bioparticles found at a particular location.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein.

What is claimed is:

1. An apparatus for identifying a biological source organism from bioparticles shed by the organism into the environment, the apparatus comprising:
   a particle collector configured to collect a sample containing a plurality of bioparticles;
   a selection and concentration system coupled to the particle collector, configured to select one or more information-rich bioparticles from the plurality of bioparticles;
   a bioparticle signature detector coupled to the selection and concentration system, the bioparticle signature detector comprising means for restricting the movement of the information-rich bioparticles and means for detecting a plurality of bioparticle signatures therefrom, wherein the bioparticle signature detector comprises a dielectrophoresis chamber for restricting movement of the one or more information-rich bioparticles, the dielectrophoresis chamber comprises an element placed within an electromagnetic field, and the element comprises an insulator or a protuberance extending from the wall of the chamber into the electromagnetic field; and
   a pattern recognition system linked to the bioparticle signature detector and configured to derive a multi-dimensional vector from the bioparticle signatures by combining bioparticle signatures and compare said multi-dimensional vector with a standard multi-dimensional vector in order to identify, from the one or more information-rich bioparticles, the biological source organism from which the bioparticles were shed.

2. The apparatus of claim 1 wherein the selection and concentration system comprises a portal configured to divert an information-rich bioparticle from a directional flow of a solution containing the plurality of bioparticles.

3. The apparatus of claim 2 wherein the portal is configured to divert the information-rich bioparticle with an electromagnetic field.

4. The apparatus of claim 1 wherein the detector comprises a panel of compounds.

5. The apparatus of claim 4 wherein the panel of compounds comprises a peptide, an antibody binding domain or molecules generated by phage display.

6. The apparatus of claim 1 wherein the means for detecting a plurality of bioparticle signatures comprises a surface plasmon resonance detector.

7. The apparatus of claim 6, wherein the surface plasmon resonance detector comprises a label-free surface plasmon resonance detector or a capillary electrophoresis surface plasmon resonance detector.

* * * * *